(12) United States Patent
Peifer et al.

(10) Patent No.: US 7,311,675 B2
(45) Date of Patent: Dec. 25, 2007

(54) SYSTEMS AND METHODS FOR MOBILE ACTIVITY MONITORING

(75) Inventors: John W. Peifer, Atlanta, GA (US); Jeff Wilson, Atlanta, GA (US); Dinal Andreasen, Marietta, GA (US); Peter Presti, Duluth, GA (US); Adam Plesh, Park Ridge, IL (US); Michael L. Jones, Marietta, GA (US); John Anschutz, Conyers, GA (US); Kevin Grogg, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 327 days.

(21) Appl. No.: 10/732,078

(22) Filed: Dec. 10, 2003

(65) Prior Publication Data

US 2005/0131318 A1   Jun. 16, 2005

(51) Int. Cl.
*A61B 5/103* (2006.01)
*A61B 5/117* (2006.01)

(52) U.S. Cl. ...................... 600/587; 600/595
(58) Field of Classification Search ........... 600/587, 600/595, 300; 128/903
See application file for complete search history.

(56) References Cited

U.S. PATENT DOCUMENTS

| | | | | |
|---|---|---|---|---|
| 5,253,656 A | | 10/1993 | Rincoe et al. | |
| 6,030,351 A | * | 2/2000 | Schmidt et al. | 600/592 |
| 6,063,046 A | * | 5/2000 | Allum | 600/595 |
| 6,165,142 A | * | 12/2000 | Bar | 600/595 |
| 6,287,253 B1 | * | 9/2001 | Ortega et al. | 600/300 |
| 6,646,556 B1 | * | 11/2003 | Smith et al. | 340/573.1 |
| 6,673,027 B2 | * | 1/2004 | Fischer | 600/595 |
| 6,915,701 B1 | * | 7/2005 | Tarler | 73/774 |
| 6,916,295 B2 | * | 7/2005 | Tasch et al. | 600/595 |
| 6,917,293 B2 | * | 7/2005 | Beggs | 340/573.1 |
| 2005/0075586 A1 | * | 4/2005 | Jamsen | 600/595 |

* cited by examiner

*Primary Examiner*—Max F. Hindenburg
*Assistant Examiner*—Jonathan M Foreman
(74) *Attorney, Agent, or Firm*—Sutherland Asbill & Brennan LLP (57) ABSTRACT

Weight-shift activity is measured by small, flat, low-cost pressure sensors placed under the cushion in the seat of the wheelchair. A wireless communications device such as a Blackberry™ page processes data received from the pressure sensors and transfers the electronic records to a central database periodically or in near real-time. The information about activity and weight shift exercises is stored at the central database where it may be accessed and viewed by Internet users. Historical records of an individual's activity may be presented to the individual and authorized caregivers through secure web pages. This activity information will encourage the wheelchair user to perform regular weight shift exercises and will allow caregivers to intervene when high-risk periods of inactivity are detected.

19 Claims, 6 Drawing Sheets

SYSTEMS AND METHODS FOR MOBILE ACTIVITY MONITORING

FIELD OF THE INVENTION

The present invention relates generally to systems and methods for mobile activity monitoring, and more particularly, to systems and methods for remotely monitoring weight-shift activity of a person seated in a wheelchair.

BACKGROUND OF THE INVENTION

When sitting for long periods of time, people must occasionally shift their weight to allow blood flow in compressed posterior tissues. Without adequate blood flow, skin problems and pressure sores can develop that lead to serious health complications. Because of their limited mobility, wheelchair users are at a greater risk to develop such sores.

One such problem, pressure ulcers, are a major public health concern that can lead to painful, life-threatening, and expensive medical complications. If severe, pressure ulcers may result in a person becoming bed-ridden. For wheelchair users, pressure ulcers can be directly attributable to the failure of a user to perform regular weight shift exercises. Weight shift exercises enable unrestricted capillary blood flow in compressed posterior tissues, and are often effective at preventing pressure ulcers and other skin problems resulting from inactivity. Unfortunately, a wheelchair user often does not realize if he or she has been stationary for extended periods of time, which may lead to sores and skin problems.

What is needed are systems and methods to enable the activity monitoring of a person seated for extended periods of time, such as wheelchair users. It would also be advantageous if such systems and methods permitted not only the wheelchair user to monitor his or her activity, but also other persons, such as physical therapists, to remotely monitor the wheelchair user's activity.

SUMMARY OF THE INVENTION

Activity monitoring systems and methods of the present invention promote healthy skin by monitoring and encouraging weight shift activity. The systems and methods of the present invention perform continuous activity measurements and use wireless data communications to provide feedback to both the wheelchair user and skin care specialists through a web-based interface.

Weight-shift activity is measured by small, flat, low-cost pressure sensors placed under the cushion in the seat of the wheelchair. A wireless communications device such as a Blackberry™ page processes data received from the pressure sensors and transfers the electronic records to a central database periodically or in near real-time. The information about activity and weight shift exercises is stored at the central database where it may be accessed and viewed by Internet users. Historical records of an individual's activity may be presented to the individual and authorized caregivers through secure web pages. This activity information encourages the wheelchair user to perform regular weight shift exercises and allows caregivers to intervene when high-risk periods of inactivity are detected.

BRIEF DESCRIPTION OF THE DRAWINGS

Having thus described the invention in general terms, reference will now be made to the accompanying drawings, which are not necessarily drawn to scale, and wherein:

DETAILED DESCRIPTION OF THE PRESENT INVENTION

The present invention now will be described more fully hereinafter with reference to the accompanying drawings, in which preferred embodiments of the invention are shown. The present invention may be adapted for use in a wide variety of applications and is suitable for any environment in which mobile activity monitoring is desired. By way of illustration and not by way of limitation, unless indicated otherwise, the preferred embodiment is presented in the context of a system and method in which weight-shift activity of a person seated in a wheelchair is monitored. This invention may be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
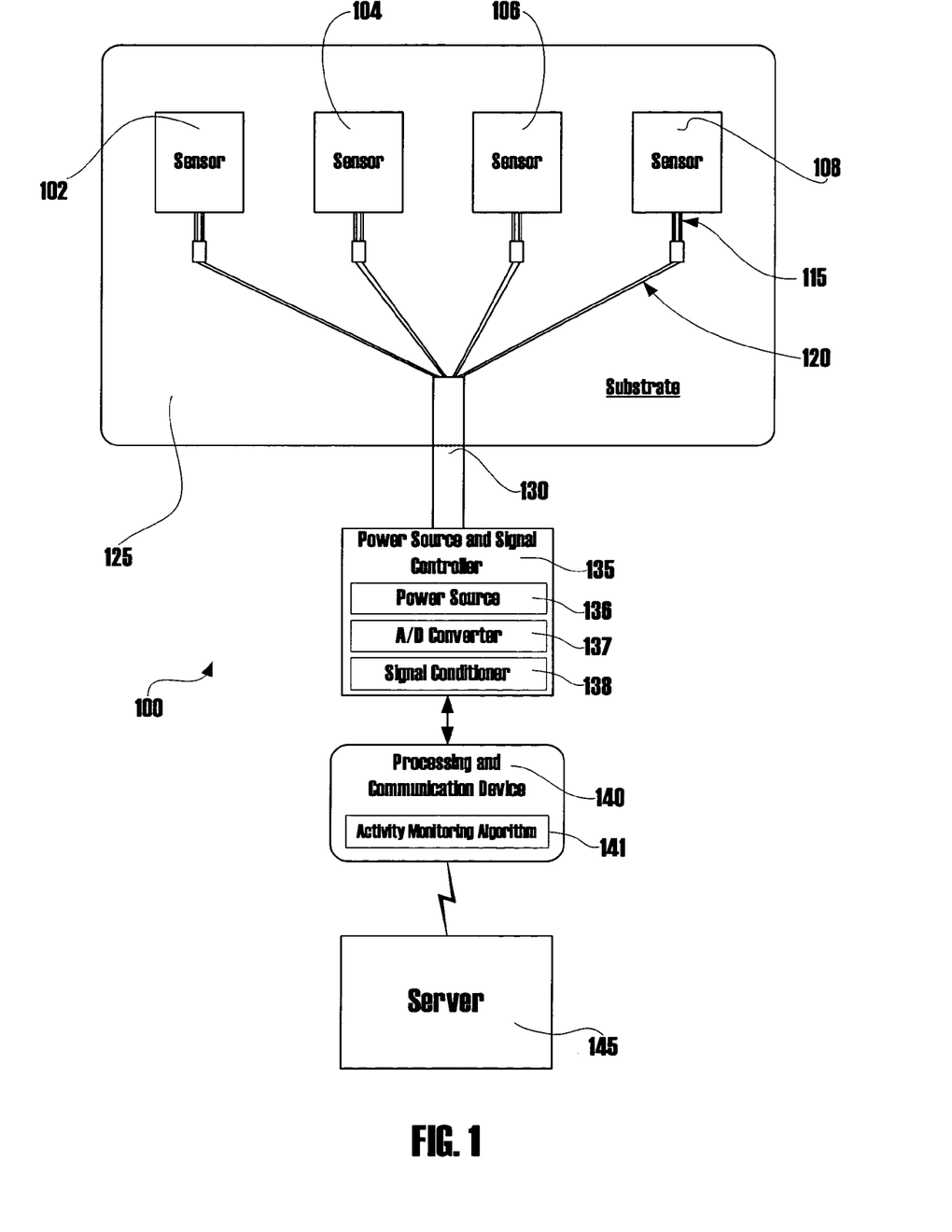
FIG. 1 is a block diagram illustrating an exemplary system in accordance with certain exemplary embodiments of the present invention.

FIG. 1 shows a block diagram illustrating an exemplary system 100 in accordance with certain exemplary embodiments of the present invention. As shown, the system 100 includes a substrate 125, a power source and signal controller 135, a processing and communication device 140, and a server 145. Attached to the substrate 125 are a plurality of sensors 102, 104, 106, 108 forming a sensor array. The sensors 102, 104, 106, 108 are each operable to transmit signals that indicate the pressure or force applied to each sensor 102, 104, 106, 108, as is known in the art. According to one aspect of the present invention, the sensors 102, 104, 106, 108 are placed in the seat, or within a cushion, underneath a seated person to monitor the amount of movement or activity of that person.

According to a preferred embodiment of the present invention, the sensors 102, 104, 106, 108 may be force sensing resistors (FSRs) that are polymer-thick film (PTF) devices that exhibit a decrease in resistance with an increase in the force applied to the active surface. When pressure is applied to the sensors 102, 104, 106, 108, the output voltage of the sensors 102, 104, 106, 108 increases due to the decrease in resistance of the FSRs with the application of pressure. Therefore, the monitoring of the voltage output of the sensors 102, 104, 106, 108 permits the system to effectively monitor the pressure applied to the respective sensors 102, 104, 106, 108. It should be appreciated that although FSRs are preferred and used as the sensors 102, 104, 106, 108 in the embodiments described herein, the sensors 102, 104, 106, 108 may also be capacitive sensors or piezoelectric pressure sensors, as are known in the art.

As illustrated in FIG. 1, each sensor 102, 104, 106, 108 may include two leads 115, which are in respective communication with two wires 120 in electrical communication with the power source and signal controller 135 for providing a continuous, low voltage source to each sensor 102, 104, 106, 108. According to one embodiment of the present invention, the sensors 102, 104, 106, 108 are Series 400 FSRs manufactured by Interlink™ having an active sensor area of 1.5" by 1.5" and a thickness of less than 0.5 mm. It will be appreciated that the FSRs may not provide a precise measure of force and variations between sensors may be as much as ±5 to 25%. A variety of external factors, such as bending and temperature, may also contribute to variability in FSR measurements.

To reduce variances in due to external factors such as bending and temperature fluctuations, the sensors 102, 104, 106, 108 are mounted on a flat substrate 125. The substrate 125 is preferably semi-rigid or rigid so as to prevent bending of the sensors 102, 104, 106, 108. According to one aspect of the invention, the substrate 125 is constructed of plastic and can lay flat in the seat of a wheelchair underneath the wheelchair's cushion. It will be appreciated that although the substrate 125 may reduce some variability in the sensors' measurements, some variability may remain. However, the variability will have little effect on the present invention, as precise pressures are unnecessary to measure activity resulting from short-term (e.g., seconds and minutes) changes in pressure, as will be explained in further detail below.

As shown in the embodiment of FIG. 1, the four sensors 102, 104, 106, 108 are mounted in a line on the substrate 125 having a approximate dimensions of 8.5 inches by 14 inches, where the sensors 102, 104, 106, 108 are mounted 1.5" from the back edge of the substrate 125 and are evenly spaced along the length of the substrate 125. According to one aspect of the invention, the semi-rigid substrate 125 may be encased between two layers of rubber sheeting (not illustrated) approximately 0.5 mm thick, where the relatively thin rubber sheeting protects the wires 120 connected to the sensors 102, 104, 106, 108 and provides the sensors 102, 104, 106, 108 protection from moisture, abrasion and sharp impacts. Other materials may be used for the encasing, including, e.g., plastic or metal.

Collectively, the sensors 102, 104, 106, 108 (including respective leads 115 and wires 120), substrate 125, and encasing materials are referred to hereinafter as a sensor pad. According to one embodiment of the present invention, the sensor pad is completely sealed except for a ribbon cable 130 that connects the sensors 102, 104, 106, 108 and substrate 125 to the power source and signal controller 135. According to one aspect of the invention, the bottom of the sensor pad may include Velcro™ or a double sided adhesive material to allow the sensor pad to be attached to or integrated with the seats of a variety of different wheelchairs.

The sensor configuration illustrated in FIG. 1 may be suited for placement in air cushions as well as foam cushions that are flexible. It will be appreciated that cushions having a rigid base may require a different sensor configuration that sits between the rigid basin and a gel cushion. Nevertheless, the sensor pad should generally be positioned in the center of a wheelchair below the ischial tuburosities of the wheelchair user. It should also be appreciated that the system 100 is designed to accommodate a variety of sensor configurations so as to provide for accurate measurements of pressure over a variety of geometries. For instance, where the system 100 of the present invention is used to monitor the activity of a person seated in a wheelchair, additional sensors may be used to more accurately monitor a person's activity. As an example, additional sensors, such as eight sensors in a 4 by 2 grid, may be advantageous for large seating areas. Other configurations, as appreciated by those of skill in the art, may also be possible.

Referring once again to FIG. 1, the system 100 is powered by the power source and signal controller 135, and more particularly, the power source 136, which provides power to the sensors 102, 104, 106, 108 and to the A/D converter 137 and signal conditioner 138 within the power source and signal controller 135. According to one embodiment of the invention, the power source 136 may comprise a stack of twelve (12) 1.5 Volt C cell batteries providing approximately 1 mA of current, although other power sources, such as batteries, known to those of skill in the art may also be used. It is preferred that the power source 136 provide power to the system 100 components for extended periods of time to reduce the need to recharge or change the power source 136.

According to one aspect of the invention, one or more voltage regulators (not illustrated) may also be placed within the power source and signal controller 135, such as in the signal conditioner 138, where the voltage regulators are operable to reduce power supplies to appropriate levels (e.g., to +1.25 VDC, −1.25 VDC) to keep a relatively low current level through the sensors 102, 104, 106, 108. For instance, where FSRs are used, one or more voltage regulators may be necessary to reduce power supplies to appropriate levels when the resistance of the FSRs decrease as a result of the application of force to the FSRs.

The A/D converter 137 receives analog voltage signals from each of the sensors 102, 104, 106, 108 and converts them to digital form. The resulting digital signals are digital pressure-indicative values. As described above, because the resistance of the sensors 102, 104, 106, 108 drops with applied pressure, for instance, from a seated person's posterior, lower resistance will result in lower voltages. Therefore, the analog values converted by the A/D converter 137 may be a measure of the voltage of each sensor, which indicates the pressure placed on each sensor where the input voltage remains constant. Prior to digitization, the measure of voltage may undergo a linearization operation, as is explained below. It will be appreciated that other related analog values, such as resistance, may also be used by the system 100 as analog pressure-indicative signals to determine the relative pressure placed on each sensor at anytime.

According to one embodiment of the present invention, the A/D converter 137 may be a DATAQ™ serial 8-bit A/D converter that requires +9 VDC and −9 VDC for operation. This power may be supplied by the power source 136. Additionally, the signal conditioner 138 may include signal conditioning electronics that include a circuit board having op-amp linearization circuitry, as is known to those of skill in the art. This may be advantageous where the sensors, such as FSRs, have non-linear response to pressure. The linearization therefore allows the resulting digitized pressure-indicative values to be linear rather than correcting a non-linear sensor response elsewhere in the system 100. Nevertheless, it will be appreciated that the linearization of analog measurements of digitized values may occur elsewhere in the system 100.

The digital pressure-indicative values are collected by the system 100 and forwarded by the power source 136 and signal controller 135 to the processing and communication device 140 at a rate of approximately four samples per second, where a sample includes a pressure-indicative value for each of the four sensors 102, 104, 106, 108. The processing and communication device 140 may include a wireless page, such as a Blackberry™ device, which is operable to communicate wirelessly with the server 145. According to an alternative embodiment of the present invention, the processing and communication device 140 may also comprise a laptop, tablet PC, personal digital assistant, or mobile phone. The processing and communication device 140 is preferably operable to process the pressure-indicative values received from the A/D converter 137 according to an activity monitoring algorithm 141 stored thereon. The activity monitoring algorithm 141 is operable to identify weight shift events based on the pressure-indicative values received from the power source and signal controller 135.

The activity monitoring algorithm 141 includes computer program instructions may be loaded onto the processing and communication device 140, which may be a general purpose computer, special purpose computer, or other programmable data processing apparatus, where the instructions which execute on the computers or other programmable data processing apparatus create means for implementing the functions described herein. Such computer program instructions may also be stored in a computer-readable memory that can direct the processing and communication device 140 to function in a particular manner. Further, the methods described herein may be embodied as a data processing system or a computer program product on a computer-readable storage medium having computer-readable program code means embodied in the storage medium. Any suitable computer-readable storage medium may be utilized including hard disks, CD-ROMs, DVDs, optical storage devices, or magnetic storage devices. Accordingly, the present invention may take the form of an entirely hardware embodiment, an entirely software embodiment or an embodiment combining software and hardware aspects, such as firmware. According to a preferred embodiment, the methods described herein are implemented by a wireless processing and communication device 140 embodied as a Blackberry™ page.

According to one embodiment of the present invention, the activity monitoring algorithm 141 averages the two left sensor pressure-indicative values (e.g., from sensors 102, 104) for each sample. The two right sensor pressure-indicative values (e.g., from sensors 106, 108) for each sample are also averaged together by the activity monitoring algorithm 141. The left and right averages are collected and stored by the processing and communication device 140 in a memory (not illustrated).

The right and left averaged pressure-indicative values are used to calculate a long term moving average used to estimate the pressure state in which an individual is seated normally without performing a shift. It will be appreciated that because a seated individual can adjust weight distribution through a wide range of movements that may or may not be associated with a weight shift event (also referred herein to a weight shift activity), it is difficult to detect what should be considered an upright and still state in all situations and environments. Therefore, the upright and still state is measured by pressure-indicative values taken in situations where the individual is seated (i.e., exerting pressure on the sensor pad) but not moving enough to register as a weight shift activity. The activity monitoring algorithm 141 therefore uses the long-term moving average as a means of approximately tracking the user's weight in a normal sitting position. This average is then used by the activity monitoring algorithm 141 to compare against continuously measured pressure-indicative values to determine when a weight shift event has taken place.

According to methods of the present invention, the system 100 attempts to detect weight shift events so that pressure-indicative values during these events can be excluded from the normal sitting long-term average. For instance, if a user executes a full shift in body weight, the activity monitoring algorithm 141 will detect a significant change in pressure for more than, e.g., a few seconds, and will not include sensor data during that event in the long-term moving average. Therefore, by using a long-term moving average, the system 100 accommodates for sensor drift and slowly changing seating posture.

For instance, if the activity monitoring algorithm 141 detects a relative change in either the left or right moving average of 50% or greater then the algorithm 141 may halt updates to the long term moving average of both the left and right pressure-indicative values. Other percentages may be used to signify a weight shift activity, although 50% or approximately 50% is preferred. It will be appreciated that a very gradual change in sensor values over the course of an hour will not trigger a 50% shift. Therefore, the halting of updates, which may also be referred to as a shift trigger, allows a seated individual to complete an activity such as a weight shift and then return to their resting seating behavior without skewing the long-term averages. A time limit of, e.g., 90 seconds is placed on the duration in which moving average updates may be halted. After this period of time, the algorithm 141 will begin to allow moving average updates. This approach allows the algorithm 141 to recover from borderline conditions that might keep the algorithm 141 in a state that consistently overestimates weight shift percentage values.

The activity monitoring algorithm 141 constantly examines recently measured left and right average pressure-indicative values to identify relative changes in those values to identify potential weight shift events. The average pressure-indicative values for each side, right and left, are continuously monitored for changes, and are compared to the corresponding long-term moving averages for each side by the algorithm 141. More specifically, the algorithm 141 calculates the difference between the average pressure-indicative value for each side by the moving average for each respective side. The algorithm 141 then normalizes the results of these comparisons to create weight shift percentage values ranging from 0 to 100%. To normalize the changes in average pressure-indicative values for each side, the algorithm 141 divides the computed differences by the difference between long-term moving average (representing full weight on the sensors during normal sitting) and the maximum observed sensor value (representing no weight on the sensors). Therefore, the normalization process maps sensor values to a 0 to 1 scale, where the sensor values when no weight is placed on a monitored chair represent one end of the scale, and the long-term sensor average with full weight in the normal sitting position represent the other end of the scale.

Because the algorithm 141 normalizes the left and right average pressure-indicative values, weight shift percentage values may be computed and reported as activity, where the weight shift percentage values represent a ratio of the pressure-indicative values to the long term moving average. This may occur in real-time, or routinely, such that weight shift percentage values for each previous ten-minute span are reported together. According to another aspect of the invention, weight shift percentage values may only be reported where there is a change in the weight shift percentage values.

Specifically, the weight shift percentage values describe the degree to which force is added or removed from the sensors related to weight changes in the seat. A weight shift percentage value of 0% describes a condition where the user is sitting stationary, and a weight shift percentage value of 100% describes the condition where the user is fully removed from the seat or shifts his or her weight fully off of one side of the seat. Although the moving average can occasionally produce weight shift percentage values above 100 and below 0, the reported shift percentage values may be held by the activity monitoring algorithm 141 to a floor and ceiling of 0% and 100% respectively.

As noted above, the activity monitoring algorithm 141 is executed on the processing and communication device 140, where a preferred processing and communication device 140 is a wireless Blackberry™ page. Because the processing and communication device 140 is operable to transmit information wirelessly, the processing and communication device 140 can wirelessly transmit weight shift percentages to a remote location. According to the preferred embodiment the page may package the algorithm-generated weight-shift percentage values into emails sent to the server 145, after which the server 145 may parse the email and insert the weight shift percentage values into a Structured Query Language (SQL) database that may be accessed by authorized users over the Internet. It will be appreciated that each weight-shift percentage value is recorded and emailed with a time stamp indicating when the weight-shift percentage value was recorded. Additionally, the server 145 may send a receipt to the page to notify that the data has been successfully received so that upon receipt of the notification the page can delete old data. If the notification receipt is not received in a timely fashion, the page may resend the data after a predetermined amount of time, such as 5 minutes. This technique ensures that no data is lost except in the case of filling up all memory on the processing and communication device 140 or a general hardware failure.

It will be appreciated that although the processing and communication device 140 is illustrated as a single component in FIG. 1, the activity monitoring algorithm 141 and associated processing hardware may be located external to the device. For instance, the activity monitoring algorithm 141 may be positioned in the power source and signal controller 135, such that the processing and communication device only functions to forward weight shift percentage values to a remote location. Similarly, the power source 136, A/D converter 137 and signal conditioner 138 may be independent hardware components that are not local to each other or disposed within a single device such as the power source and signal controller 135.

It will be appreciated that the system 100 of the present invention does not need to measure actual seat pressures in known units of force. The system only uses the pressure-indicative values received from the power source and signal controller 135 to determine weight shift percentage values, which are reported as activity. As a result, the system 100 does not need to be calibrated to an individual seating condition (weight, position, posture). Furthermore, the variations of different cushions in which the sensor pad may be placed will have no affect on the system and method of the present invention, although differing cushions and locations of the sensor pad may result in varying degrees of spreading and absorbing of the forces exerted by the user's weight. The advantage of the normalizing approach is that the system 100 will effectively identify weight shift activity in a variety of conditions including variability in the cushions, actual user weight and weight distribution, ambient temperature, barometric pressure, battery voltage, etc. The system 100 can detect both long periods of inactivity, and any type of movement reported as an activity.

Figure 2:
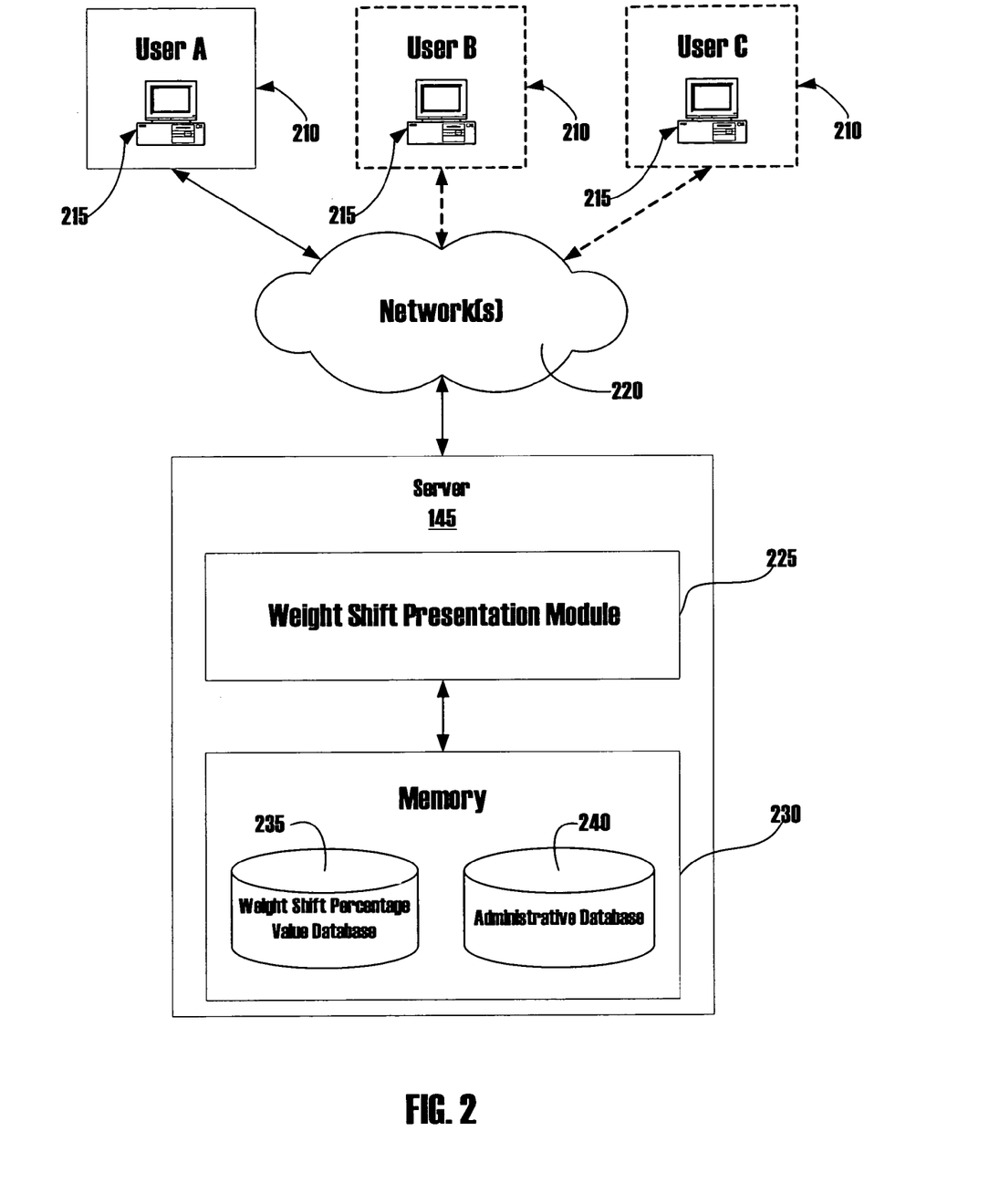
FIG. 2 is a block diagram of one or more users in communication with a mobile activity monitoring module, according to one embodiment of the present invention.

Using the systems and methods of the present invention both wheelchair users and caregivers can monitor the activity data. FIG. 2 shows a plurality of users 210 in communication with the server 145 via one or more networks 220, such as a LAN, or a WAN such as the Internet. The users communicate with the server 145 via a computer 215 associated with each user. Therefore, the users 210 may monitor the weight shift activity of a person remotely, and in the preferred embodiment, from any computer with Internet access to the server 145. According to one aspect of the present invention, the users may be the person whose activity is being monitored, a physical therapist, doctor, family member, or any other individual who may wish to monitor the weight shift activity of a seated person.

As noted above, weight shift percentage values are stored by the server 145, such as in a weight shift percentage values database 235 within the server's memory 230. This database 235 may be a SQL database, as is known in the art, and may store the weight shift percentage values for a length of time, such as a week or month, such that historical weight shift activity data is maintained. The users 210 may view the weight shift percentage values within the database 235 using the weight shift presentation module 225, which is a program that permits the uses 210 to access and view a graphical display of the weight shift percentage values for a monitored person over a period of time such as a day. Like the activity monitoring algorithm 141, the weight shift presentation module 225 may be implemented by computer program instructions executed in conjunction with a processor and computer program instructions of the server 145.

As described with respect to FIGS. 4 and 5 below, the weight shift presentation module 225 of the present invention may present the weight shift percentage values for a particular monitored person using one or more graphical presentations, including activity graphs in polar, bar and/or line form. These values may also be presented in non-graphical form, such as in a table of values. Because each weight-shift percentage value is received from the processing and communication device 140 with a time and date stamp identifying the time and date the values were calculated, the weight shift presentation module 225 can provide detailed information on a person's activity during specific times of a day.

According to another aspect of the invention, access to the weight shift percentage values may be permitted by the weight shift presentation module 225 only after a user 210 has logged in using an established user-id and password, to prevent unauthorized access to the weight shift percentage values of a particular person. Furthermore, each user may have varying rights to view data. For instance, a person being monitored may only be able to view graphs representing recent weight shift activity, whereas a physical therapist or system administrator may be able to access all historical weight shift percentage values for a particular monitored person. Furthermore, the user-id and password may be used to identify persons with rights to access an administrative database 240, which may be used to store user accounts and other administrative information for operating the server 145.

Figure 3:
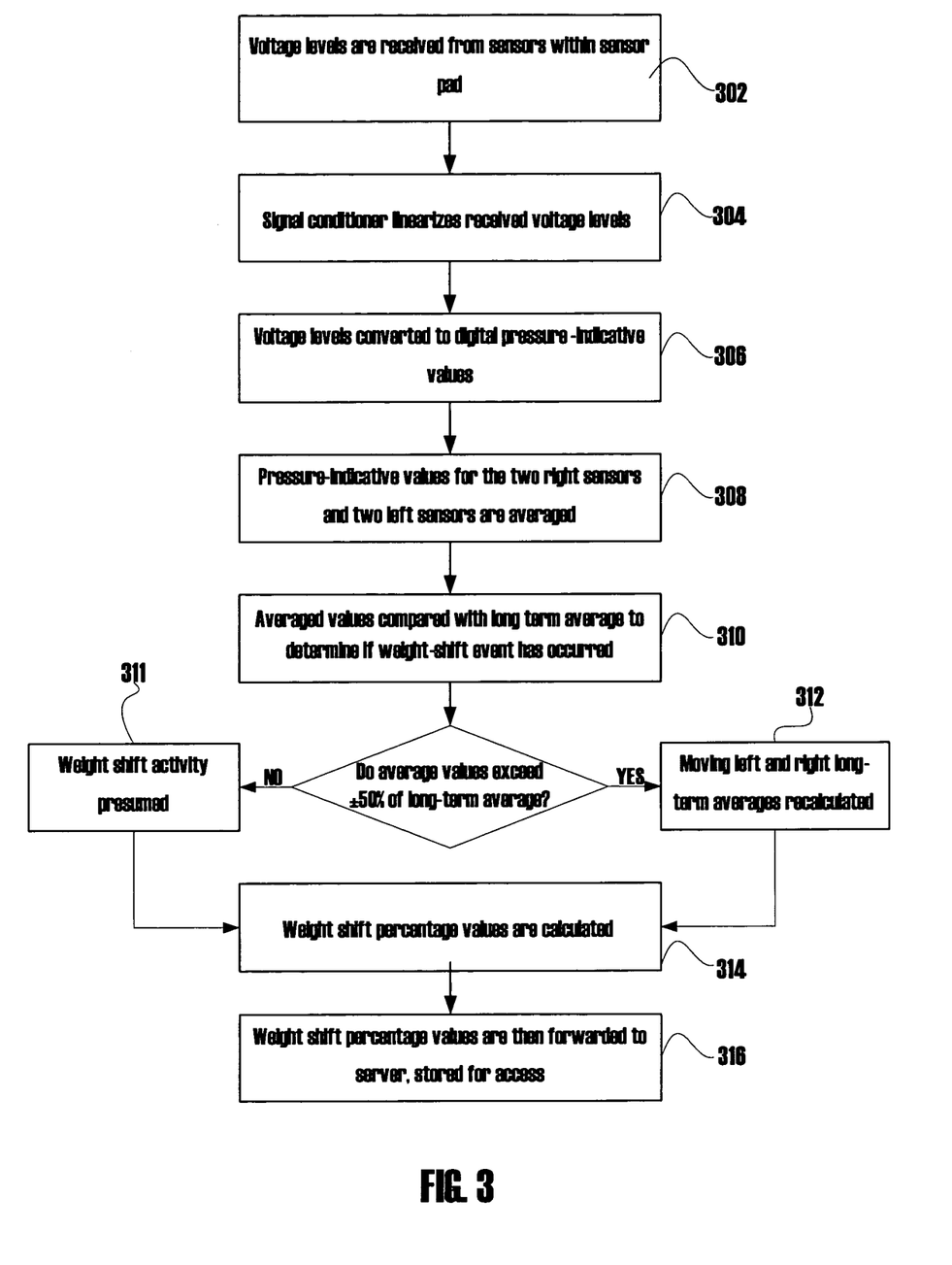
FIG. 3 is a block diagram flowchart showing a mobile activity reporting process, according to one embodiment of the present invention.

Next, FIG. 3 shows a block diagram flowchart showing a mobile activity reporting process, according to an illustrative embodiment of the present invention. First, voltage levels are received (block 302) from the sensors 102, 104, 106, 108 within the sensor pad, which is placed within a cushion on which a person is seated. The signal conditioner 138 may then linearize the voltage levels (block 304), which are then converted to digital pressure-indicative values by the A/D converter 137 (block 306). The pressure-indicative values for the two right sensors and two left sensors are averaged (block 308), respectively, and are then compared the long term average of these values to determine if a weight-shift event has occurred (block 310). If the newly measured average values represent a relative change in either the left or right moving average of 50%, a weight shift activity is presumed to have taken place and the newly measured average values are not used to recalculate the moving average (block 311). On the other hand, if the newly measured average values do not represent a significant change, the values are used to recalculate the moving left and right long-term averages (block 312). Next, weight shift percentage values are calculated using the long-term average (block 314). The weight shift percentage values are then forwarded to the server, where they are stored for access by one or more users via graphical interfaces (block 316).

Figure 4:
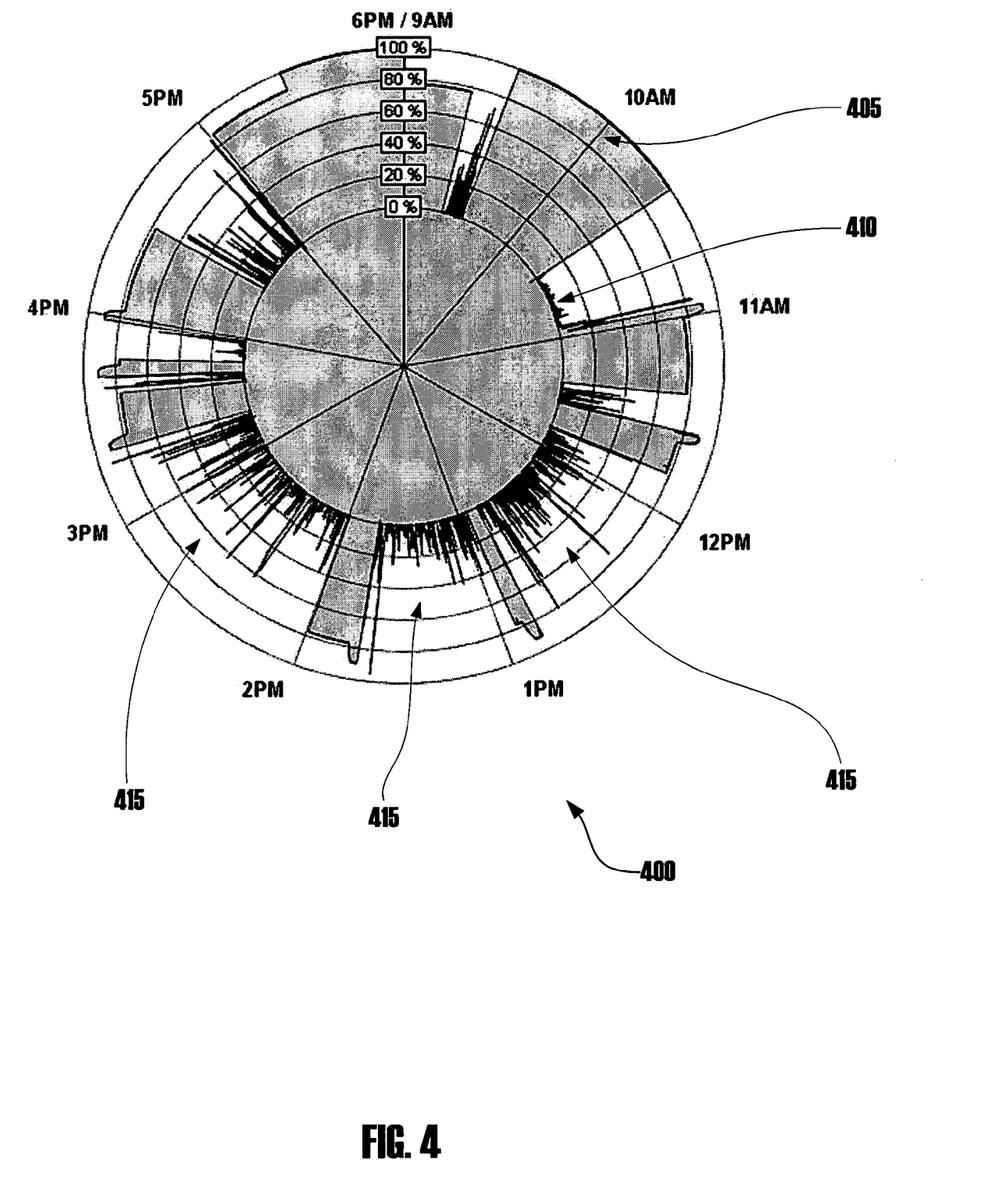
FIG. 4 is a polar plot illustrating the weight shift percentage of a person during various times of a day, according to an illustrative example of one embodiment of the present invention.
Figure 5:
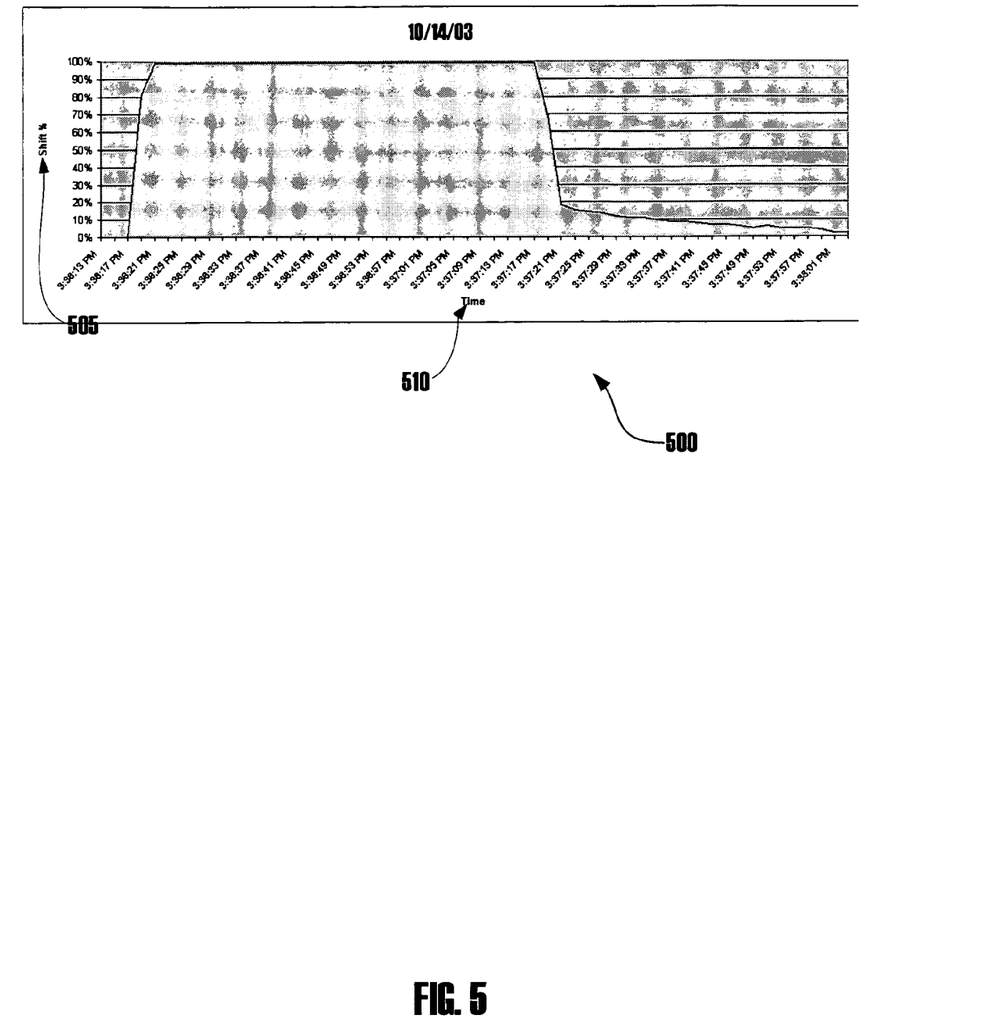
FIG. 5 is a graph showing a maximum shift percentage of a person during various times of a day, according to an illustrative example of one embodiment of the present invention.

FIG. 4 shows a polar plot 400 illustrating the weight shift activity of a person during various times of a day, according to an illustrative example of one embodiment of the present invention. The polar plot 400 may be generated by the weight shift presentation module 225 illustrated in FIG. 2, and may be presented to one or more users in remote or local communication with the server 145. Therefore, the polar plot 400 may be made available to both wheelchair users and caregivers. According to one embodiment of the invention, the monitored time presented on the plot 400 may be configurable by viewers using simple and intuitive user interfaces.

The polar plot 400 is intended to present a quick overview of seating activity over the course of a day. As illustrated in the polar plot in FIG. 4, long periods of inactivity and the times at which these occur can be easily identified. For instance, at approximately 10 am 405, the person is removed from his or her seat, where as at approximately 10:45 am 410 the user is in the seat and not moving. The spikes in the polar graph 415 illustrate times when the weight shift percentage values fluctuate, illustrating movement or activity of the person in the seat.

The weight shift presentation module 225 may also present a caregiver a more detailed look at the weight shift activity in the form of spreadsheet-formatted data, which may permit the caregiver to examine subtler changes weight shift activity. For instance, as shown in FIG. 5, weight shift percentage values 505 graphed with respect to time 510, such as every 4 seconds, may be monitored by a caregiver using a shaded line graph 500.

Figure 6:
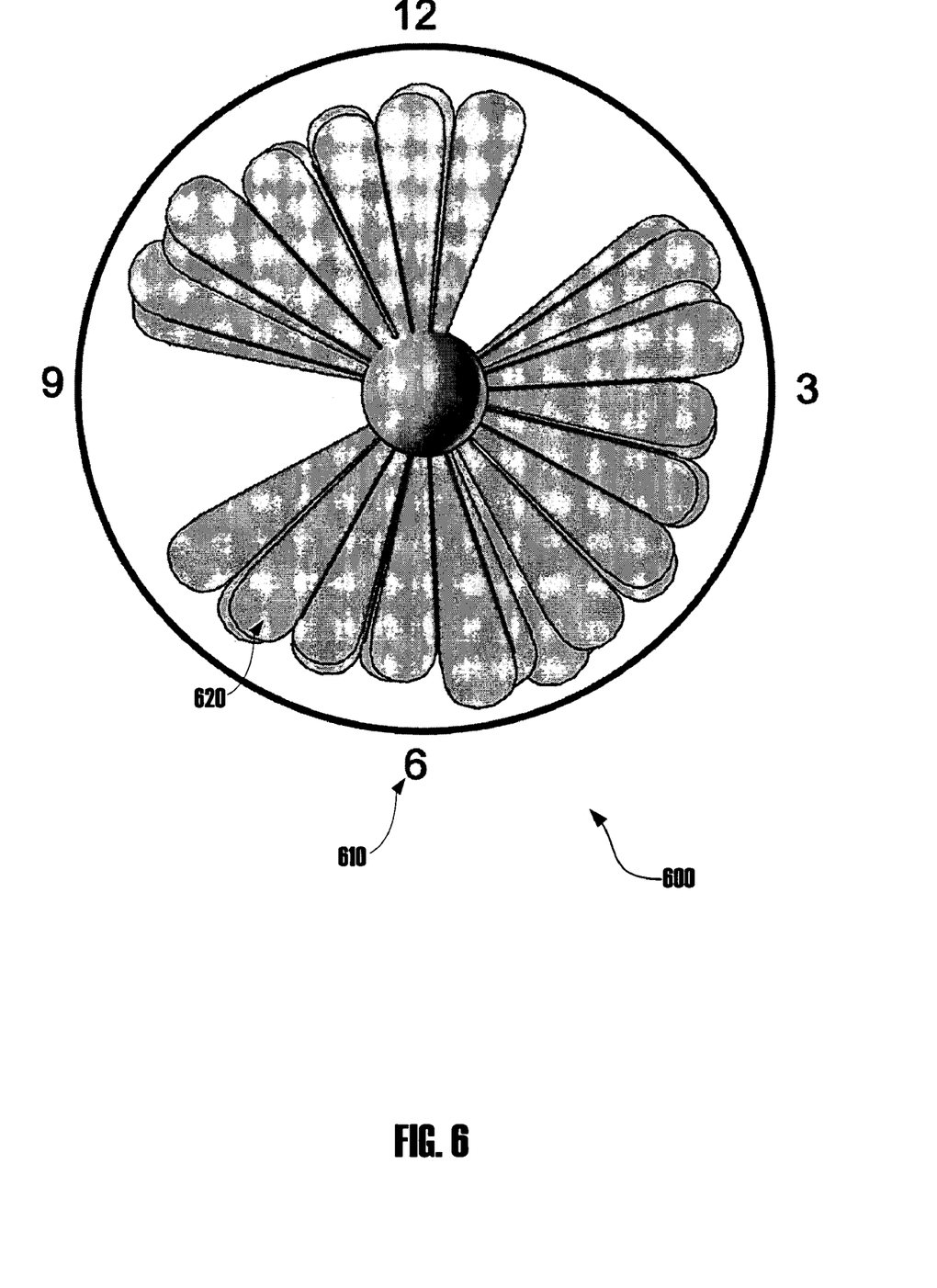
FIG. 6 is a daisy plot illustrating the weight shift percentage of a person during various times of a day, according to an illustrative example of one embodiment of the present invention.

Yet another graphical display of weight shift activity generated by the weight shift presentation module 225 is illustrated in FIG. 6, according to an illustrative example of the present invention. FIG. 6 shows a daisy plot 600, which is a simple graphical display that allows a user to quickly ascertain periods of inactivity. The daisy plot 600 includes a plurality of the petals 620 having various petal lengths, where the petals 620 represent activity and the petal lengths represent the amount of weight shift activity, or the weight shift percentage value, for a particular time of day. Missing petals represent inactivity. The daisy plot 600 preferably includes times 610 to identify when periods of activity and inactivity take place, and the daisy plot 600 may correspond to a 12 hour time period or a 24 hour day.

A healthy daisy plot would show full petals throughout the day. When petals are short or missing, a user can tell at a glance when period of low activity are occurring. Because of the simple nature of the daisy plot 600, it may be advantageous for presenting to a non-technical wheelchair user to quickly identify healthy activity patterns and at risk periods of inactivity. Therefore, in viewing the daisy plot 600 the wheelchair user can receive feedback on his or her weight shift activity to encourage regular weight shifts.

Additional features of the present invention may include the reporting and monitoring of individual sensors, rather than composite weight shift percentage values. Furthermore, the present invention may be used to monitor other activity, such as activities of infants in an ICU, patients in a hospital or nursing home bed, or other environments in which activity monitoring may be useful.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A system for activity monitoring, comprising:
   a sensor array comprising at least one sensor, wherein the sensor array transmits at least one analog signal indicative of the pressure applied to the at least one sensor;
   an analog-to-digital (A/D) converter, wherein the A/D converter receives the at least one analog signal and generates at least one digital signal indicative of the pressure applied to the at least one sensor;
   a processing device, in communication with the A/D converter, wherein the processing device:
   receives the at least one digital signal indicative of the pressure applied to the at least one sensor;
   converts the at least one digital signal into at least one pressure-indicative value;
   determines if a weight shift occurs at least in part by determining a difference between the at least one pressure-indicative value and at least one moving average of pressure-indicative values; and
   generates a weight shift percentage value, wherein the weight shift percentage value is based at least in part on the determined difference; and
   communicates the weight shift percentage value to a server in wireless communication with the processing device.

2. The system of claim 1, wherein the server presents the weight shift percentage value to at least one user via a graphical display.

3. The system of claim 1, wherein the processing device communicates the weight shift percentage value to the server via email.

4. The system of claim 1, wherein the processing device is a wireless page.

5. The system of claim 1, wherein the processing device generates the weight shift percentage value based at least in part on a normalization of the determined difference.

6. The system of claim 1, wherein the processing device recalculates the at least one moving average of pressure-indicative values using the at least one pressure-indicative value.

7. The system of claim 6, wherein the processing device does not recalculate the at least one moving average of pressure-indicative values if a weight shift occurs.

8. The system of claim 1, wherein the sensor array is placed on a semi-rigid sensor substrate.

9. The system of claim 8, wherein the semi-rigid sensor substrate is encased in at least two layers of encasing material.

10. The system of claim 9, wherein the encasing material comprises rubber.

11. A system for activity monitoring, comprising:
- a sensor array comprising at least one sensor, wherein the sensor array transmits at least one analog signal indicative of the pressure applied to the at least one sensor;
- an analog-to-digital (A/D) converter, wherein the A/D converter receives the at least one analog signal and generates at least one digital signal indicative of the pressure applied to the at least one sensor;
- a processing device, in communication with the A/D converter, wherein the processing device:
  - receives the at least one digital signal indicative of the pressure applied to the at least one sensor;
  - converts the at least one digital signal into at least one pressure-indicative value;
  - determines if a weight shift occurs at least in part by determining a difference between the at least one pressure-indicative value and at least one moving average of pressure-indicative values; and
  - generates a weight shift percentage value, wherein the weight shift percentage value is calculated at least in part by a normalization of the determined difference; and
- a communication device in wireless communication with a server, wherein the communication device communicates the weight shift percentage value to the server.

12. The system of claim 11, wherein the server presents the weight shift percentage value to at least one user via a graphical display.

13. The system of claim 11, wherein the processing device communicates the weight shift percentage value to the server via email.

14. The system of claim 11, wherein the processing device is a wireless page.

15. The system of claim 11, wherein the processing device recalculates the at least one moving average of pressure-indicative values using the at least one pressure-indicative value.

16. The system of claim 15, wherein the processing device does not recalculate the at least one moving average of pressure-indicative values if a weight shift occurs.

17. The system of claim 11, wherein the sensor array is placed on a semi-rigid sensor substrate.

18. The system of claim 17, wherein the semi-rigid sensor substrate is encased in at least two layers of encasing material.

19. The system of claim 18, wherein the encasing material comprises rubber.

* * * * *